(12) United States Patent  
Gerder (10) Patent No.: US 11,672,937 B2  
(45) Date of Patent: Jun. 13, 2023

(54) COOLING ELEMENT, CONTROL SYSTEM, FREEZING HOLDING DEVICE AND PROCESS FOR CONTROLLING A CLOSED-CIRCUIT RESPIRATOR

(71) Applicant: Dräger Safety AG & Co. KGaA, Lübeck (DE)

(72) Inventor: Henning Gerder, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 842 days.

(21) Appl. No.: 16/717,098

(22) Filed: Dec. 17, 2019

(65) Prior Publication Data

US 2020/0188626 A1 Jun. 18, 2020

(30) Foreign Application Priority Data

Dec. 18, 2018 (DE) ...................... 10 2018 009 805.3

(51) Int. Cl.
| | |
|---|---|
| *A61M 16/10* | (2006.01) |
| *A61M 16/00* | (2006.01) |
| *A61M 16/08* | (2006.01) |
| *A62B 9/00* | (2006.01) |

(52) U.S. Cl.
CPC .... *A61M 16/1075* (2013.01); *A61M 16/0003* (2014.02); *A61M 16/022* (2017.08); *A61M 16/0891* (2014.02); *A62B 9/003* (2013.01); *A61M 2205/3368* (2013.01); *A61M 2205/3382* (2013.01); *A61M 2205/3386* (2013.01);

(Continued)

(58) Field of Classification Search
CPC .. A61M 16/00; A61M 16/0003; A61M 16/10; A61M 16/1075; A61M 16/14; A61M 16/022; A61M 16/0891; A61M 2205/127; A61M 2205/3368; A61M 2205/36; A61M 2205/3606; A61M 2205/3646; A61M 2205/366; A61M 2205/3382; A61M 2205/3379; A61M 2205/3386; A61M 2209/04; A62B 9/00; A62B 9/003; B63C 11/24; F28D 1/0233
See application file for complete search history.

(56) References Cited

U.S. PATENT DOCUMENTS 4,294,244 A * 10/1981 Pasternack ............... A62B 7/10  
607/108  
4,440,162 A 4/1984 Sewell et al.  
(Continued)

FOREIGN PATENT DOCUMENTS

CN 1864298 A 11/2006  
CN 101489657 A 7/2009  
(Continued)

*Primary Examiner* — Colin W Stuart  
(74) *Attorney, Agent, or Firm* — McGlew and Tuttle, P.C.

(57) ABSTRACT

A cooling element for use within a cooling device of a closed-circuit respirator, includes an element housing, which has a liquid-tight cap and is filled with a coolant, which has a melting point below 50° C., especially below 45° C., preferably below 40° C. A sensor element is arranged in contact with the coolant within the element housing such that the sensor element can be moved in a direction of the gravity acting on the sensor element in the liquid state of the coolant during the use of the closed-circuit respirator by a user of the closed-circuit respirator.

18 Claims, 7 Drawing Sheets

(52) U.S. Cl.
CPC .............. *A61M 2205/366* (2013.01); *A61M 2205/3606* (2013.01)

(56) References Cited

U.S. PATENT DOCUMENTS

| | | | |
|---|---|---|---|
| 6,523,538 B1 * | 2/2003 | Wikefeldt | A61M 16/0808 128/205.12 |
| 6,563,417 B1 | 5/2003 | Shaw | |
| 6,847,912 B2 | 1/2005 | Forster | |
| 6,953,919 B2 | 10/2005 | Clothier | |
| 2006/0254587 A1 | 11/2006 | Berry et al. | |
| 2010/0108063 A1 * | 5/2010 | Koch | A61M 16/1075 128/204.15 |
| 2015/0007820 A1 * | 1/2015 | Koch | A62B 19/00 128/204.15 |
| 2016/0213879 A1 * | 7/2016 | Parthasarathy | A61M 16/208 |
| 2018/0202362 A1 | 7/2018 | Bintz et al. | |
| 2018/0249860 A1 | 9/2018 | Doglioni Majer | |
| 2019/0184212 A1 | 6/2019 | Cheesman et al. | |

FOREIGN PATENT DOCUMENTS

| | | |
|---|---|---|
| CN | 102442761 A | 5/2012 |
| CN | 203249672 U | 10/2013 |
| CN | 203499796 U | 3/2014 |
| CN | 103958417 A | 7/2014 |
| CN | 104005317 A | 8/2014 |
| CN | 104568655 A | 4/2015 |
| CN | 105971698 U | 9/2016 |
| CN | 107290503 A | 10/2017 |
| CN | 108966612 A | 12/2018 |
| CN | 108981850 A | 12/2018 |
| DE | 29511467 U1 | 9/1995 |
| DE | 102006058164 B3 | 10/2007 |
| DE | 102011014267 A1 | 9/2012 |
| DE | 102016005076 A1 | 11/2017 |

* cited by examiner

COOLING ELEMENT, CONTROL SYSTEM, FREEZING HOLDING DEVICE AND PROCESS FOR CONTROLLING A CLOSED-CIRCUIT RESPIRATOR

CROSS REFERENCE TO RELATED APPLICATIONS

This application claims the benefit of priority under 35 U.S.C. § 119 of Application 10 2018 009 805.3, filed Dec. 18, 2018, the entire contents of which are incorporated herein by reference.

TECHNICAL FIELD

The present invention pertains to a cooling element for use within a cooling device of a closed-circuit respirator, to a control system for controlling a breathing gas circuit in a closed-circuit respirator, and to a freezing holding device for at least one cooling element. The present invention pertains, furthermore, to a process for cooling a cooling element for use in a cooling device of a closed-circuit respirator and to a process for controlling a breathing gas circuit in a closed-circuit respirator.

TECHNICAL BACKGROUND

The coolant is preferably ice or a coolant configured as a Phase Change Material (PCM), which is used within a liquid battery in the closed-circuit respirator.

In preparation for the use of the closed-circuit respirator, a quantity of oxygen that is carried along in a pressurized gas cylinder of the closed-circuit respirator, a dimensioning of a carried-along quantity of lime for a $CO_2$ absorber and a quantity of coolant in the cooling device are typically adapted to one another. Such an adaptation takes place, taking into consideration necessary safety reserves while striving for weight optimization at the same time.

SUMMARY

An object of the present invention is to provide an improved control of a closed-circuit respirator, especially an improved control of the cooling device in a closed-circuit respirator.

According to the present invention, a cooling element is provided according to a first aspect of the present invention for accomplishing this object for use within a cooling device of a closed-circuit respirator with an element housing and with a sensor element.

The element housing has a liquid-tight cap and is filled with a coolant, which has a melting point below 50° C., especially below 45° C., preferably below 40° C., especially preferably in a melting point range between 30° C. and 35° C.

The sensor element is arranged in contact with the coolant within the element housing such that the sensor element is movable in the direction of gravity acting on the sensor element in the liquid state of the coolant during the use of the closed-circuit respirator by a user of the closed-circuit respirator.

The present invention is based on the discovery that the usability of the cooling device of the closed-circuit respirator, especially the remaining duration of use thereof, can be estimated especially well by checking the temperature of the inhaled gas during a mission. Furthermore, it was recognized within the framework of the present invention that the temperature can be checked by checking the state of aggregation of the coolant within the cooling device. To check the state of aggregation, a sensor element, which is movable in the cooling element filled with coolant, especially a sensor element sinking during the movement or floating during the movement, is provided according to the present invention, at the position of which sensor element the state of aggregation of the coolant can be detected.

The solution according to the present invention advantageously makes it possible to estimate a temperature within the breathing gas circuit during the use of the closed-circuit respirator on the basis of the state of aggregation of the coolant. In addition to the known checking of the consumed quantity of oxygen in the pressurized gas cylinder, an additional, important parameter of the closed-circuit respirator can consequently be monitored with the temperature of the breathing gas. In particular, the sensor element advantageously makes it possible to forecast a future development of the temperature of the inhaled gas, as a result of which a future duration of use can advantageously be predicted.

The temperature curve of the inhaled gas provided over the duration of use typically depends very much on the time, at which the melting point of the coolant is reached. Consequently, the fact that the time of reaching the melting point can be detected is especially advantageous for the determination of a change in the state of aggregation according to the present invention. As a result, it is possible to check whether the melting point of the coolant is reached at a time forecasted before the use of the closed-circuit respirator. If this is the case, the maximum duration of use forecasted before the mission can likewise be assumed to be predicted for the mission. If there is a deviation between the actual reaching of the melting point and the forecast, the benchmark data forecasted before the mission, for example, maximum duration of use, can still be correspondingly adapted during the mission.

A further advantage is the especially simple integration of the cooling element according to the present invention in existing closed-circuit respirators. In the simplest case, only the sensor element would have to be inserted into an already known element housing. In this case, the analysis of the position of the sensor element may already be possible, for example, by an optical analysis of the position of the sensor element.

Movability of the sensor element in the direction of the gravity acting on the sensor element is preferably achieved via a correspondingly provided inner volume of the element housing. Thus, the inner volume according to the present invention is enclosed by the element housing such that a movement of the sensor element in the direction of the acting gravity is possible due to the action of gravity and of the buoyancy force within the liquefied coolant. This movement is advantageously possible essentially between a housing bottom of the element housing and a coolant surface of the liquefied coolant. In this case, the longer a path that the sensor element covers in the presence of the change in the state of aggregation, the less prone to error is a corresponding detection of this movement possible.

According to the present invention, this movability of the sensor element makes possible a movement of the sensor element between a starting position present in the frozen state of the coolant and a final position present in the liquid state of the coolant within the element housing.

Preferred embodiments of the cooling device according to the present invention will be described below.

The coolant is water is an especially preferred embodiment of the present invention. The coolant can be provided in an especially cost-effective manner in this embodiment. Furthermore, water especially advantageously makes possible a free movement of the sensor element corresponding to the gravity and the buoyancy force presently acting on the sensor element. In an alternative or additional embodiment, the coolant is at least partially a PCM coolant with a melting point below 50° C., especially below 45° C., especially preferably in a melting point range between 30° C. and 35° C.

In an advantageous embodiment, the sensor element is configured to sink to a housing bottom of the element housing due to the gravity acting on the sensor element in the liquid state of the coolant. In this embodiment, the sensor element is configured such that the acting gravity is greater than the buoyancy force opposing the gravity within the coolant. During a cooling of the coolant below the melting point of the coolant, the sensor element must therefore be held within an area of the element housing, which area is located opposite the housing bottom. The change in state of aggregation from solid to liquid during the use of the closed-circuit respirator can consequently be recognized by a sinking of the sensor element to the housing bottom.

In another embodiment, the sensor element is configured to float on a coolant surface of the coolant due to a buoyancy force of the sensor element, which buoyancy force acts against gravity, in the liquid state of the coolant. The sensor element is configured in this embodiment such that the acting gravity is lower than the buoyancy force opposing the gravity within the coolant. During a cooling of the coolant below the melting point of the coolant, the sensor element must be held in the area of the housing bottom. The change in state of aggregation from solid to liquid during the use of the closed-circuit respirator can consequently be recognized by a rising of the sensor element (in a direction of gravity—namely counter to the force of gravity) from the housing bottom to the coolant surface.

In another embodiment, the sensor element is arranged movably only in a central area of the coolant which is different from the coolant surface and the housing bottom. As a result, a movement of the sensor element between a starting position present in the frozen state of the coolant and a final position present in the liquid state of the coolant can be especially precisely detected, since there are few positions between the starting position and the final position of the sensor element within the element housing, so that a leaving of the starting position also essentially indicates a reaching of the final position.

In an advantageous embodiment, the sensor element has a passive RFID tag. As a result, a position and/or a change in the position of the sensor element can especially advantageously be determined in a contactless manner. In addition, an optical analysis of the position of the sensor element is consequently not necessary. Furthermore, an RFID tag can be installed in the sensor element in an especially cost-effective manner. The transmission of data for a passive RFID tag typically takes place such that an electromagnetic field generated by an RFID reader supplies the passive RFID tag with energy and is modulated in a data-dependent manner by the RFID tag. The configuration of a passive RFID tag is known and will therefore not be explained in detail below. Reference shall herewith be made to the publications U.S. Pat. No. 6,563,417 B1, U.S. Pat. No. 6,847,912 B2 and U.S. Pat. No. 6,953,919 B2 only as examples for a representation of the function and typical use of RFID technology (U.S. Pat. No. 6,563,417 B1, 6,847,912 B2 and 6,953,919 B2 are incorporated herein by reference).

Furthermore, the contactless position determination by means of RFID tag makes it possible that an additional electronic unit of the closed-circuit respirator can be arranged in a single area, which is preferably protected by a separate housing against a physical or thermal impact during the use of the closed-circuit respirator.

In another advantageous embodiment, the sensor element has a permanent magnet. The contactless determination of a change in position and/or of a position of the sensor element is advantageously possible, as a result, for example, by means of a reed relay or a Hall sensor. In a preferred variant of this embodiment, the sensor element is arranged in direct proximity to a housing wall of the element housing of the cooling element. As a result, in spite of a typically short range of a magnetic interaction, a measurement of the change in position and/or of the position of the sensor element is advantageously made possible by a position outside of the cooling element. The measurement of the position and/or change in position of the sensor element can be achieved in an especially cost-effective manner via a magnetic interaction.

In an especially advantageous embodiment of the cooling element according to the present invention, the element housing has, furthermore, a housing guide, which is arranged within the cooling element at the element housing and which is configured to limit the movability of the sensor element in the coolant in the liquid state of the coolant such that the sensor element is movable only in the direction of the gravity acting on the sensor element during the use of the closed-circuit respirator by a user of the closed-circuit respirator. Such a housing guide can be produced in a simple and cost-effective manner. Furthermore, the housing guide can advantageously prevent an undesired sticking of the sensor element within the element housing by the movement of the sensor element within the element housing being limited in a predefined manner. The element housing and the housing guide are configured together as one piece in a preferred variant. This can be brought about, for example, within the framework of an injection molding process. To be movable only in the direction of gravity means within the framework of this embodiment that the housing guide can allow a certain lateral movement component of the sensor element based on the shaping of the cooling element, but that such a lateral movement always brings about a movement component in the direction of gravity.

In a preferred variant of the previous embodiment, the cooling element has, moreover, an additional sensor element and an additional housing guide, the sensor element being configured and arranged such that the sensor element sinks to a housing bottom of the element housing in the liquid state of the coolant due to gravity acting on the sensor element within a movement channel formed by the housing guide, and the additional sensor element being configured and arranged such that it floats on the coolant surface of the coolant in the liquid state of the coolant due to a buoyancy force of the sensor element, which buoyancy force acts against gravity, within an additional movement channel formed by the additional housing guide. The reaching of the melting point of the coolant with the corresponding change in the state of aggregation can be detected in an especially reliable manner by two sensor elements moving in opposite directions to each other. Thus, for example, a detection is avoided because of an inhomogeneously melting coolant by the housing guide and the additional housing guide being configured in two different areas of the cooling element. The reaching of the melting point in this case is considered to be reliably detected only if a corresponding movement from a starting position was detected for both sensor elements. In this embodiment, an erroneous detection of the melting point can, furthermore, be avoided because of a sensor element being stuck to the element housing.

In another embodiment, the cooling element has a plurality of sensor elements, wherein the plurality of sensor elements are arranged such that they are movable in the direction of the gravity acting on the sensor element in the liquid state of the coolant during the use of the closed-circuit respirator by a user of the closed-circuit respirator.

The element housing of the cooling element is configured as wedge-shaped in another embodiment. A holding of the cooling element as well as an insertion or removal of the cooling element into the element housing or from the element housing are consequently possible in a simple manner, since, for example, slipping off at surfaces of the cooling element that are parallel to each other is avoided.

According to a second aspect of the present invention, the object according to the present invention is accomplished by a control system for checking a breathing gas circuit in a closed-circuit respirator, which has a cooling device, in which at least one cooling element in accordance with at least one of the above embodiments according to the first aspect of the present invention is arranged in a device housing of the cooling device. Furthermore, the control system according to the present invention has at least one detection unit and a control unit.

The at least one detection unit is arranged outside of the cooling element in the closed-circuit respirator and the at least one detection unit is configured to determine position information and to output a corresponding position signal, which implies, in particular indicates, the position information, the position information being information related to a current position of the sensor element in the element housing of the cooling element.

The control unit is arranged outside of the cooling device in the closed-circuit respirator and is connected to the detection unit for signaling. Furthermore, the control unit is configured to receive the position signal, to determine the corresponding position information and to determine a coolant state of the cooling device based on the position information, wherein the coolant state indicates an expected, further cooling time of the cooling device, and wherein the control unit is, furthermore, configured to output a control signal based on the coolant state. The control signal is preferably suitable for triggering a control output at a user interface of the closed-circuit respirator.

The control system according to the second aspect of the present invention advantageously makes it possible to determine a position and/or a change in position of the sensor element via the detection unit and to analyze same via the control unit. In comparison to an embodiment of the cooling element according to the present invention according to the first aspect of the present invention, in which the position of the sensor element is analyzed optically, the control system according to the present invention is especially convenient and allows an automated recognition of a movement of the sensor element.

The determination of the coolant state makes possible an especially advantageous output of the control signal since the coolant state can be directly inferred from the control signal without further analysis.

The control system according to the present invention comprises the cooling element according to the present invention and hence all the advantages of this cooling element.

The detection unit and the control unit may be arranged spaced apart from one another or within a single processing module.

Preferred embodiments of the control system according to the present invention will be described below.

In an especially preferred embodiment, the determined coolant state indicates a state of aggregation of the coolant. In this connection, it is especially indicated whether the coolant is solid or liquid. The temperature curve of the inhaled gas provided by the closed-circuit respirator plotted over a mission time is typically greatly dependent on the time, at which the melting point of the coolant used is reached. Therefore, the control system according to this embodiment makes possible an especially precise checking of whether the melting point was reached at a forecasted time during the mission, or whether the temperature curve to be expected must be changed compared to the respective forecast. As a result, an expected, further cooling time can be indicated especially accurately during the use of the closed-circuit respirator.

In an especially preferred variant of the previous embodiment, the determined coolant state indicates a movement of the sensor element from a starting position of the sensor element known for the frozen coolant within the cooling element. In this case, a positional difference between a current position of the sensor element and the starting position is preferably determined by means of the detection unit with cooled, i.e., unconsumed coolant at the beginning of the use of the closed-circuit respirator. Consequently, a beginning of a melting process of the coolant can especially advantageously be accurately detected. In an example of this variant, it is detected at regular time intervals whether the sensor element is present within the known starting position, and if this is no longer the case during a detection, a corresponding control signal is triggered by the control unit. In another example of this variant, the presence of the sensor element in an area adjacent to the starting position is detected, and a corresponding control signal is subsequently triggered by the control unit. The detection of a leaving of the starting position advantageously allows the detection of a single event, which is independent of a path of the sensor element within the cooling element. As a result, only a small quantity of information needs to be transmitted. In addition, the detection of a single event is less prone to error than the detection of a series of events.

In another advantageous embodiment, the determined coolant state indicates a movement of the sensor element into a final position of the sensor element, which final position is known for the fully melted coolant within the cooling element. In this case, a positional difference between a current position of the sensor element and the known final position in the cooling element is preferably determined by means of the detection unit with a then melted, i.e., consumed or partially consumed coolant. An end of a melting process of the coolant can especially advantageously be accurately detected as a result. In an example of this variant, it is detected at regular time intervals whether the sensor element is present within the known final position, and if this is the case during a detection, a corresponding control signal is triggered by the control unit. In another example of this variant, the presence of the sensor element is detected in an area of the cooling element, which area is adjacent to the final position, and a corresponding control signal is subsequently triggered by the control unit. The detection of a reaching of the final position advantageously allows the detection of a single event, which is independent of a path of the sensor element within the cooling element. As a result, little information has to be transmitted. In addition, the detection of a single event is less prone to error than the detection of a series of events.

In another embodiment, the control system has a plurality of detection units, wherein the control unit is configured to determine a corresponding plurality of pieces of position information from a corresponding plurality of position signals and to determine the coolant state from the plurality of pieces of position information based on a determined movement of the sensor element. In the control system according to this embodiment, it can be advantageously ensured that a melting of the coolant is not already detected if only a small area of the coolant is melted because of inhomogeneities within the cooling device. Furthermore, the control unit in this embodiment is capable of determining a transition area between a solid state of the coolant and a melted state of the coolant especially accurately, since a position of the sensor element between the starting position and the final position indicates a not yet fully melted coolant. A position of the sensor element between the starting position and the final position indicates especially a percentage, by which the coolant has already melted.

In a preferred embodiment, the sensor element has a passive RFID tag, the at least one detection unit being configured as an RFID reader. The sensor element may consequently be arranged at a distance of several decimeters from the detection unit. The provision of a central electronic unit of the closed-circuit respirator, in which the detection unit is arranged, is made possible as a result. Such a central electronic unit is preferably protected by a corresponding housing against physical or thermal stress. Furthermore, existing RFID systems can be integrated into the control system according to the present invention in an especially simple and cost-effective manner. The precise configurations of the RFID tag and the RFID reader are known from the publications cited above, among others, and will not be further explained below.

The sensor element has a permanent magnet, wherein the at least one detection unit is configured as a reed relay or as a Hall sensor in another embodiment of the control system according to the present invention. As a result, a certain distance between the sensor element and the detection unit is advantageously made possible. The control system according to this embodiment has in a variant a plurality of detection units, the control unit being configured to determine a plurality of pieces of position information from a corresponding plurality of position signals. The plurality of detection units corresponding to a path is advantageously arranged at the cooling device or in the cooling device between a predefined starting position and a predefined final position of the sensor element. In this variant, in spite of the short distance of the magnetic interaction with the sensor element, the coolant state and hence the expected, further cooling time of the cooling device can be determined directly.

According to a third aspect of the present invention, the object according to the present invention is accomplished by a freezing holding device for at least one cooling element according to at least one of the embodiments mentioned. The freezing holding device has a frame and a positioning magnet.

The frame has at least one receptacle for the at least one cooling element, wherein the receptacle is arranged such that the cooling element with liquid coolant inserted into the receptacle allows a movement of the sensor element in the direction of the gravity acting on the sensor element.

The positioning magnet is arranged at the frame in the area of the receptacle such that the sensor element is held in a starting position in the liquid state of the coolant via a magnetic force acting between the positioning magnet and the sensor element, which starting position is different from a final position that the sensor element assumes within the cooling element in the liquid state of the coolant during the use of the closed-circuit respirator by a user of the closed-circuit respirator. In this case, the freezing holding device is suitable for being arranged within a suitable freezing device and to make possible a fixing of the sensor element in the starting position due to the positioning magnet during a freezing time of a freezing process for freezing the coolant of the cooling element.

The freezing holding device according to the third aspect of the present invention advantageously allows a freezing of the sensor element in a starting position, which is different from the position that the sensor element assumes in the presence of a liquid coolant. The freezing holding device according to the third aspect of the present invention therefore allows the provision of the cooling element according to the present invention in such a frozen state as it is necessary for operating the control system according to the present invention. A movement of the sensor element from the starting position into the final position upon reaching the melting point of the coolant can first be determined by the positioning of the sensor element provided via the freezing holding device.

The positioning magnet is preferably arranged at a bottom plate or at a top plate of the freezing holding device. An arrangement in the bottom plate is especially advantageous in the variant in which the sensor element is configured to float on a coolant surface of the coolant due to a buoyancy force acting against the gravity in the liquid state of the coolant. An arrangement of the positioning magnet at the top plate is, in turn, especially advantageous in the variant in which the sensor element is configured to sink to the housing bottom of the element housing due to the gravity acting on the sensor element in the liquid state of the coolant.

In the embodiment in which the positioning magnet is arranged at the top plate of the freezing holding device, the top plate is mounted movably between an open position and a closed position at the frame of the freezing holding device. In this case, the top plate is configured such that insertion of the cooling element into the receptacle is possible only in the presence of the open position, the positioning magnet being arranged in relation to the receptacle only in the presence of the closed position such that the sensor element is held in the starting position. Such a mounting of the positioning magnet advantageously allows the insertion of the cooling element into the receptacle such that the sensor element is brought into the starting position by magnetic interaction within the cooling element by the positioning magnet within the framework of the freezing movement of the cooling element into the receptacle.

According to a fourth aspect of the present invention, a process is provided for cooling a cooling element for use in a cooling device of a closed-circuit respirator to accomplish the object according to the present invention. The process according to the present invention has the following steps in this case:

provision of a sensor element within a cooling element of a cooling device of the closed-circuit respirator, which cooling element is filled with coolant;

arrangement of the sensor element in a starting position, which is different from a final position that the sensor element assumes within the cooling element in the liquid state of the coolant during the use of the closed-circuit respirator by a user of the closed-circuit respirator; and cooling of the cooling element such that the coolant is cooled to below a coolant melting point, while the sensor element remains in a sensor element starting position.

The process according to the fourth aspect of the present invention advantageously makes possible a provision of the cooling element with frozen coolant such that the sensor element is arranged in the predefined starting position within the cooling element.

According to a fifth aspect of the present invention, a process for controlling a breathing gas circuit in a closed-circuit respirator is provided to accomplish the object according to the present invention. The process according to the present invention has the following steps in this case:

insertion of the cooling element, which was cooled according to the process according to the fourth aspect of the present invention, into the cooling device of the closed-circuit respirator;

determination of position information and outputting of a corresponding position signal, which implies the position information, wherein the position information is information related to a current position of the sensor element in the cooling element;

receipt of the position signal, determination of the corresponding position information, and determination of a coolant state of the cooling device based on the position information, wherein the coolant state indicates an expected, further cooling time of the cooling device; and outputting of a control signal based on the coolant state.

The process according to the present invention according to the fifth aspect of the present invention is carried out by the control system according to the second aspect of the present invention. It therefore has all the advantages of the control system according to the present invention.

In an especially preferred embodiment, the determined coolant state indicates a state of aggregation of the coolant. In an advantageous variant of this embodiment, the determined coolant state indicates a movement of the sensor element from the starting position of the sensor element, which starting position is known for the frozen coolant within the cooling element. In an additional or alternative variant of the embodiment, the determined coolant state indicates a movement of the sensor element into a final position of the sensor element, which final position is known for the fully melted coolant within the cooling element.

In another embodiment of the process according to the present invention, the process comprises the determination of a plurality of pieces of position information and a corresponding outputting of a plurality of position signals, wherein the process comprises, furthermore, a receipt of the plurality of pieces of position information and the determination of the coolant state. In this case, the coolant state is based on a movement of the sensor element, which movement is determined based on the plurality of pieces of position information.

The present invention shall now be explained in more detail on the basis of advantageous exemplary embodiments, which are schematically shown in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1A:
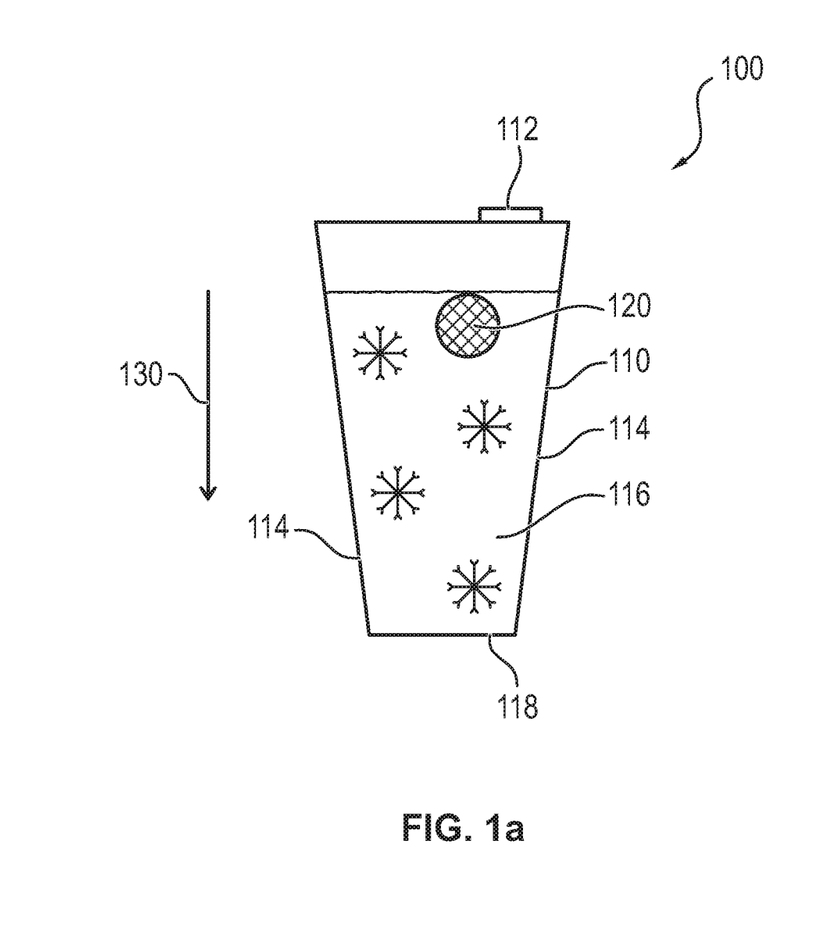
FIG. 1a is a schematic view of a first exemplary embodiment of a cooling element according to a first aspect of the present invention, wherein the cooling element is shown before reaching the melting point with a frozen coolant.
Figure 1B:
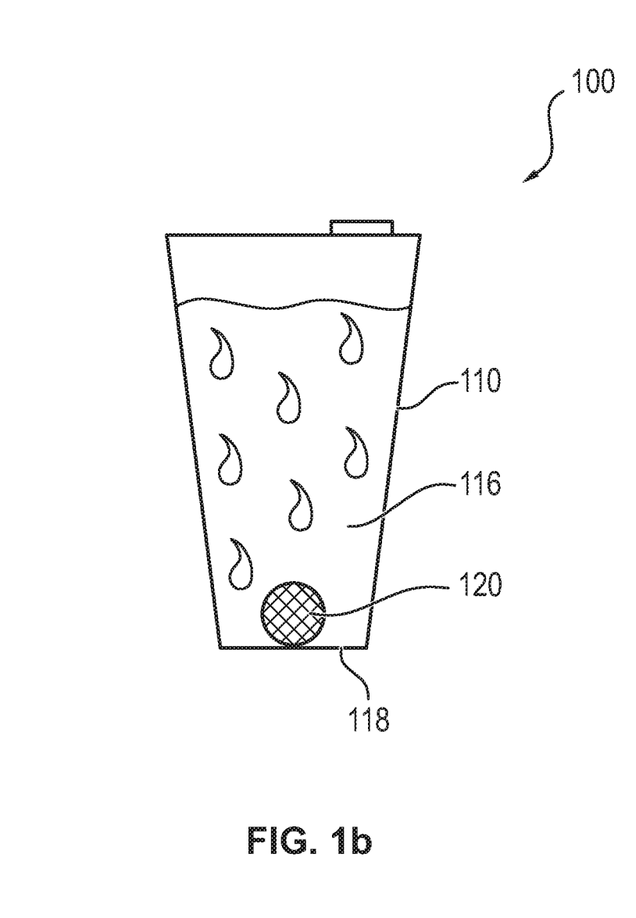
FIG. 1b is a schematic view of a first exemplary embodiment of a cooling element according to a first aspect of the present invention, wherein the cooling element is shown after reaching the melting point with a liquid coolant.

Referring to the drawings, FIGS. 1a and 1b show a respective schematic view of a first exemplary embodiment of a cooling element 100 according to a first aspect of the present invention, wherein the cooling element 100 is shown before reaching the melting point with a frozen coolant 116 (FIG. 1a) and after reaching the melting point with a liquid coolant 116 (FIG. 1b).

FIG. 1a shows the cooling element 100 according to the present invention, which is intended for use within a cooling device of a closed-circuit respirator. The cooling element 100 has an element housing 110, which has a liquid-tight cap 112 and side walls 114 tapering towards each other in a wedge-shaped manner. In the present embodiment, the cap 112 is a cap permanently closed via a weld seam. The cap is a cap which cannot be permanently closed, especially a screw cap, in one exemplary embodiment, not shown. The element housing 110 is filled with a frozen coolant 116, which has a melting point below 50° C., especially below 45° C., preferably below 40° C. The coolant 116 is water in the present embodiment. The coolant consists at least partially of a PCM-based coolant in one exemplary embodiment, not shown. The element housing 110 is not fully filled with the coolant 116 in order to allow a heat-related expansion of the coolant within the element housing 110.

Moreover, the cooling element comprises a sensor element 120 that is arranged within the element housing 110 in contact with the coolant 116. In this case, the sensor element 120 is arranged within the element housing 110 such that the sensor element 120 is movable in the liquid state of the coolant 116 in the direction of the gravity 130 acting on the sensor element 120 during the use of the closed-circuit respirator by a user of the closed-circuit respirator. Furthermore, the sensor element 120 is configured such that the sensor element 120 sinks to a housing bottom 118 of the element housing 110 in the liquid state of the coolant 116, as shown in FIG. 1b. Therefore, the weight of the sensor element 120 is greater than the buoyancy force of the sensor element 120 in water or in the other possible coolants 116. In the exemplary embodiment shown, the sensor element 120 is a metal ball. The state of the sensor element 120 shown in FIG. 1a, which shows the sensor element 120 in a predefined starting position for the use according to the present invention in the cooling device, must be prepared in a suitable manner before the beginning of the freezing of the cooling element (cf. FIGS. 5 and 6), so that the sensor element 120 does not sink to the housing bottom 118 before the freezing.

FIG. 1b shows the cooling element according to the present invention of the first exemplary embodiment which is likewise shown in FIG. 1a in a state in which the coolant 116 is melted. Because of the melting, the sensor element 120 has sunk from the starting position shown in FIG. 1a to a predefined final position on a housing bottom 118 of the element housing 110. Hence, the coolant 116 was heated to beyond its melting point during the use.

In a state, not shown, of the coolant 116, in which it was heated into the range of its melting point, the coolant 116 is partially melted, so that the sensor element 120 is not in the starting position shown in FIG. 1a and also not in the final position shown in FIG. 1b, but rather in an intermediate position located between these two positions.

Figure 2A:
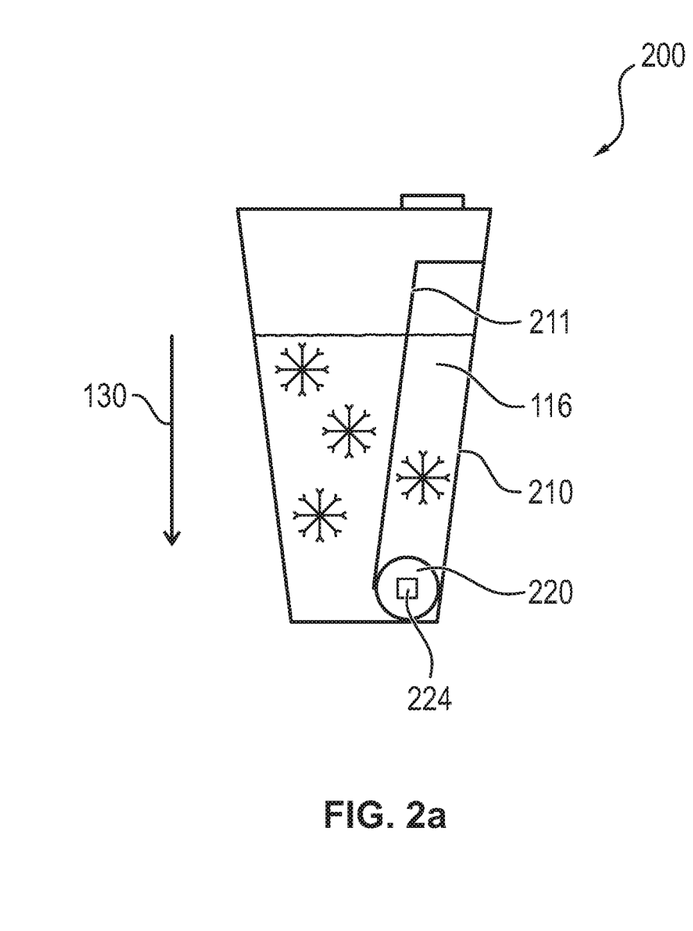
FIG. 2a is a schematic view of a second exemplary embodiment of the cooling element according to the first aspect of the present invention, wherein the cooling element is shown before reaching the melting point with a frozen coolant.
Figure 2B:
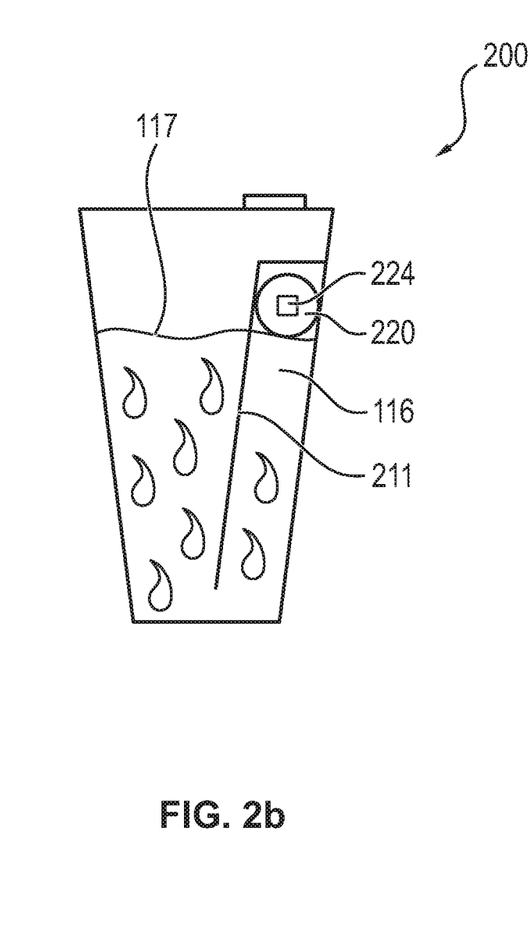
FIG. 2b is a schematic view of a second exemplary embodiment of the cooling element according to the first aspect of the present invention, wherein the cooling element is shown after reaching the melting point with a liquid coolant.

FIGS. 2a and 2b show a schematic view of a second exemplary embodiment of the cooling element 200 according to the first aspect of the present invention, wherein the cooling element 200 is shown before reaching the melting point with a frozen coolant 116 (FIG. 2a) and after reaching the melting point with a liquid coolant 116 (FIG. 2b).

The cooling element 200 differs from the cooling element 100 shown in FIGS. 1a and 1b by the element housing 210 additionally having a housing guide 211. The housing guide 211 is arranged within the cooling element 200 and is configured to limit the movability of the sensor element 220 in the coolant 116. The movability is limited in the liquid state of the coolant 116 such that the sensor element 220 is movable only in the direction of the gravity 130 acting on the sensor element 220 during use of the closed-circuit respirator by a user of the closed-circuit respirator. Being movable only in the direction of the gravity 130 means that a movement along the housing guide 211 in the present embodiment may have and also has a lateral component because of the shaping of the cooling element 200, but that each movement of the sensor element 200 also brings about a movement in the direction of the gravity 130 because of the housing guide. The housing guide 211 is formed in one piece together with the element housing 210 in the present embodiment.

By contrast to the sensor element 120 shown in FIG. 1a and FIG. 1b, the sensor element 220 is configured such that the sensor element 220 floats on a coolant surface 117 of the coolant 116 in the liquid state of the coolant 116 due to a buoyancy force between the coolant in the liquid state and the sensor element 220, which buoyancy force acts against the gravity 130. In the present embodiment, the sensor element 220 has a wedge-shaped and hollow configuration. In the frozen state of the coolant 116 shown in FIG. 2a, the sensor element is in a predefined starting position, as it typically is at the beginning of the use of the closed-circuit respirator. A melting of the coolant 116 leads to the sensor element 220 moving out of the sensor element 220 starting position due to a coolant and sensor element 220 buoyancy force against the acting gravity 130. After a full melting of the coolant 116, the sensor element 220 has assumed a sensor element final position on the coolant surface 117, which sensor element final position is predefined by the housing guide 211.

Furthermore, the sensor element 220 has a passive RFID tag 224. Via the passive RFID tag 224, a position of the sensor element 220 can especially advantageously be read by a correspondingly configured reader at a distance of over several decimeters from the cooling element 200.

In one exemplary embodiment, not shown, the sensor element comprises, furthermore, a temperature sensor. In addition to position information, temperature information can consequently be outputted. This makes possible an especially accurate determination of the coolant state.

Figure 3:
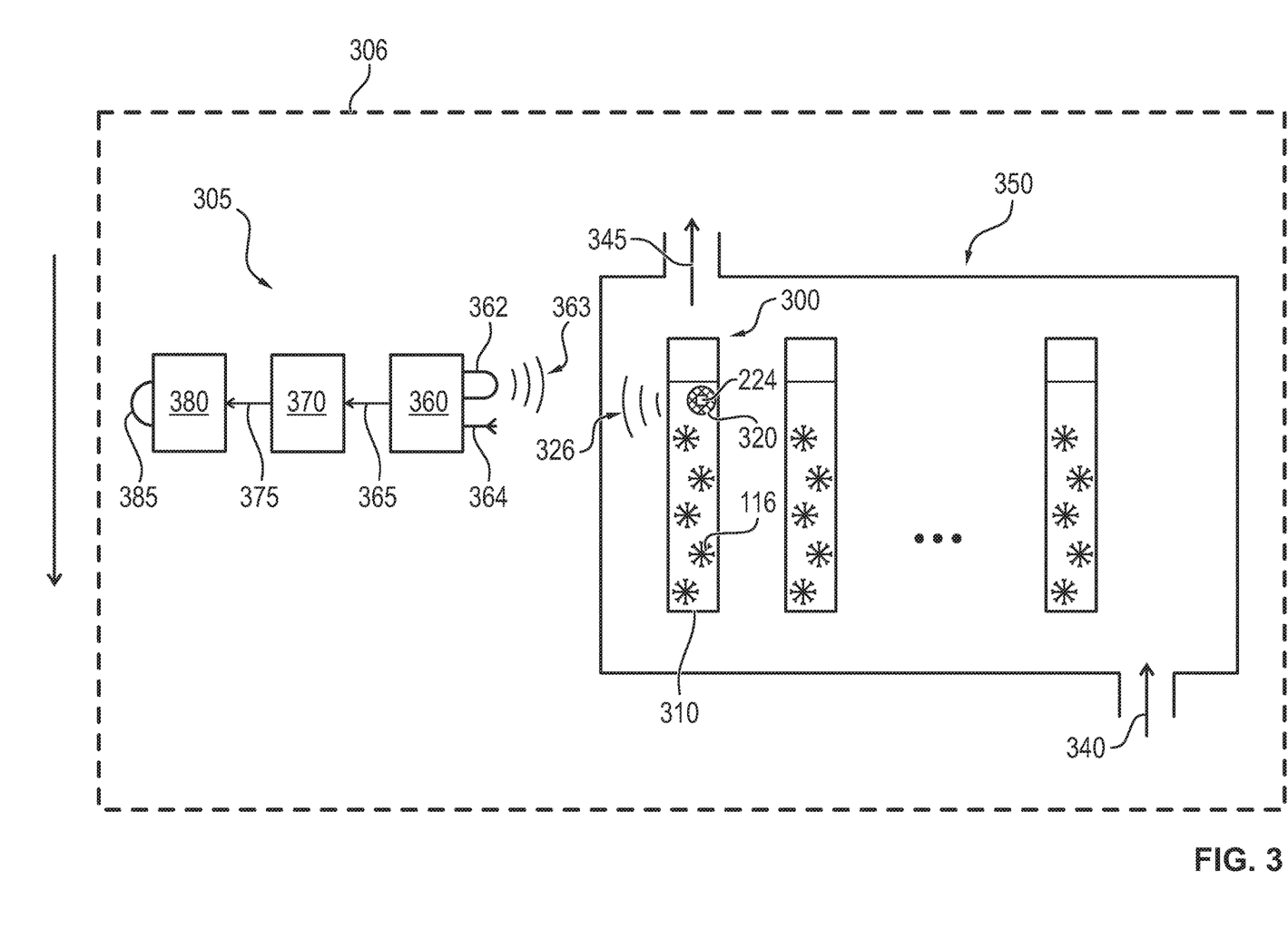
FIG. 3 is a schematic view of a first exemplary embodiment of a control system according to a second aspect of the present invention.

FIG. 3 shows a schematic view of a first exemplary embodiment of a control system 305 according to a second aspect of the present invention.

The control system 305 is configured for controlling a breathing gas circuit 340 in a closed-circuit respirator 306. The closed-circuit respirator 306 has for this purpose a cooling device 350, which has at least one cooling element 300 according to the present invention with a sensor element 320. The closed-circuit respirator 306 may comprise a housing surrounding a component space with several breathing components as disclosed in U.S. Patent Application Publication 2019/0184212, which is hereby incorporated by reference in its entirety.

It is known that the cooling device 350 within a closed-circuit respirator 306 is configured to cool the breathing gas circuit 340, which was typically heated up by a $CO_2$ absorber, not shown, by the coolant 116 located in the cooling element 300 before the breathing gas is provided as inhaled gas 345 to the user of the closed-circuit respirator 306.

In addition to the cooling element 300 according to the present invention, the control system 305 according to the present invention has, furthermore, at least one detection unit 360 and a control unit 370.

The detection unit 360 according to the present invention is arranged in the closed-circuit respirator 306 outside of the cooling element 300, and furthermore, outside of the cooling device 350 in the present embodiment, and is configured to determine position information corresponding to a current position of the sensor element 320 in the element housing 310 of the cooling element 300 and to output this position information as a position signal 365. In the present embodiment, the determination of the position information is carried out via a transmitting device 362 and an antenna device 364 of the detection unit 360. The detection unit 360 is configured as an RFID reader above the antenna device 364 and the transmitting device 362, while the sensor element 320 has a passive RFID tag 224. A corresponding information signal 326 is triggered by the sensor element 320 via a read signal 363 of the transmitting device 362 of the detection unit 360. The information signal 326 has position information related to a position of the sensor element in relation to the detection unit 360. In the present embodiment, the information signal 326 has, furthermore, identification information, which allows a clear association between the information signal and the sending sensor element. This is especially advantageous if the control system has a plurality of sensor elements. The information signal has only position information in another exemplary embodiment, not shown.

Within the framework of RFID technology, the information signal 326 is triggered as is known such that the electromagnetic field provided as a read signal 363 by the RFID reader is modulated by the passive RFID tag 224, the passive RFID tag being fed with energy that is needed for the modulation from the electromagnetic field. The detection unit 360 configured as an RFID reader is, in turn, configured to receive this modulation and hence the information signal 326 via the antenna device 364.

The control unit 370 is arranged outside of the cooling device 350 in the closed-circuit respirator 306 and is connected to the detection unit 360 for signaling. In the present embodiment, this connection for signaling is provided in a cable-based manner. Furthermore, the control unit 370 is configured to receive the position signal 365, to determine the corresponding position information and to determine a coolant state of the cooling device 350 on the basis of the position information and to output a corresponding control signal 375. The coolant state indicates an expected, further cooling time of the cooling device 350. The coolant state especially indicates a state of aggregation of the coolant 116 in the present embodiment.

The control unit 370 in the present embodiment analyzes on the basis of the position information whether a movement of the sensor element 320 has taken place. A movement of the sensor element 320 especially implies a movement of the sensor element 320 from a known starting position within the frozen coolant 116. Therefore, the detection of a movement of the sensor element 320 makes it possible to determine an incipient melting of the coolant 116. In one exemplary embodiment, not shown, the control unit analyzes on the basis of the position information whether a permanent end of this movement has started after the starting of a movement of the sensor element. Based on the incipient end of the movement, the movement of the sensor element into a known final position of the sensor element within the cooling element can be inferred, which indicates an at least almost full melting of the coolant. In another exemplary embodiment, the control unit is configured to analyze from the position information both the start of the movement of the sensor element and the permanent end of this movement and to determine a corresponding coolant state.

The movement of the sensor element from its known starting position indicates the start of a melting process of the coolant, whereas the movement of the sensor element into a known final position indicates that the coolant is almost fully melted. An intermediate path of the sensor element within the cooling element is likewise determined as position information in one example, not shown.

In another exemplary embodiment, not shown, a plurality of cooling elements of the cooling device are configured as cooling elements according to the present invention with a corresponding sensor element.

In the exemplary embodiment shown, the closed-circuit respirator 306 has, furthermore, an output unit 380 as a user interface, which is configured to provide an optical output corresponding to the coolant state corresponding to the control signal 375 via an optical output medium 385. The output unit 380 in the present embodiment is configured to output an optical output if the sensor element 320 has left the known starting position within the cooling element 300.

Figure 4:
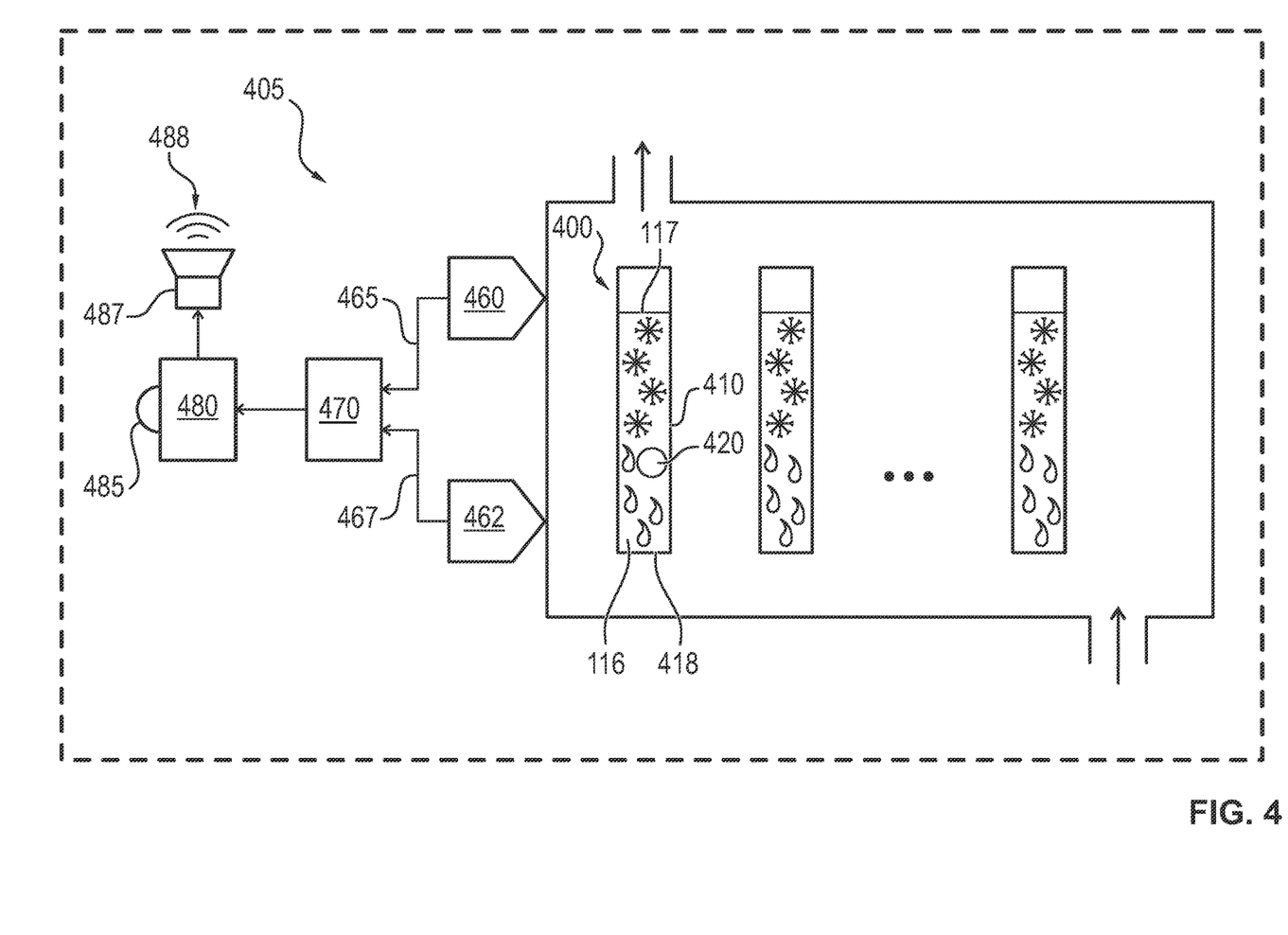
FIG. 4 is a schematic view of a second exemplary embodiment of the control system according to a second aspect of the present invention.

FIG. 4 shows a schematic view of a second exemplary embodiment of the control system 405 according to the second aspect of the present invention.

The control system 405 shown differs from the control system 305 shown in FIG. 3 by the sensor element 420 being configured to float on a coolant surface 117 of the coolant 116 due to its buoyancy force within the coolant in case of a present liquid state of the coolant 116. A state, in which the coolant is partially melted, is shown in this case, so that the sensor element 420 is located between a starting position present in the frozen state and a final position present in the melted state of the coolant 116. Furthermore, the sensor element differs by having no RFID tag, but rather is formed by a permanent magnet.

Correspondingly, the detection unit 460 differs by not being configured as an RFID reader, but rather it determines position information of the sensor element 420 configured as a permanent magnet as a reed relay or as a Hall sensor, as a reed relay in the present embodiment. For this purpose, in addition to the detection unit 460 in the exemplary embodiment shown, the control system 405 also has a second detection unit 462. The second detection unit 462 is configured to indicate the movement of the sensor element 420 from the known starting position within the cooling element 400. The first detection unit 460 is configured to indicate the movement of the sensor element 420 into the known final position of the sensor element 420 within the cooling element 400. Corresponding to the configuration of the sensor element 420, the starting position is located on the housing bottom 418 of the element housing 410 of the cooling element 400. The final position will be in the almost fully melted state of the coolant 116 on the coolant surface 117.

The control unit 470 is configured in this case to receive a corresponding plurality of position signals 465, 467 and to determine the coolant state from the corresponding pieces of position information.

In one exemplary embodiment, not shown, the control system according to the present invention has at least one additional detection unit. A percentage of a coolant melted at the current time of a mission can be inferred as a result. Thus, a position of the sensor element in the middle between the starting position and the final position indicates that already about half of the coolant is melted. A position of the sensor element at one-third of the distance between the starting position and the final position correspondingly indicates that about one-third of the coolant has melted.

A next difference between the exemplary embodiments shown in FIG. 3 and FIG. 4 is that the output unit, which is configured as a user interface, has an acoustic output medium 487 in addition to an optical output medium 485. Correspondingly, the output unit 480 is configured to output an optical output and/or an acoustic output 488 corresponding to the currently present coolant state.

Figure 5:
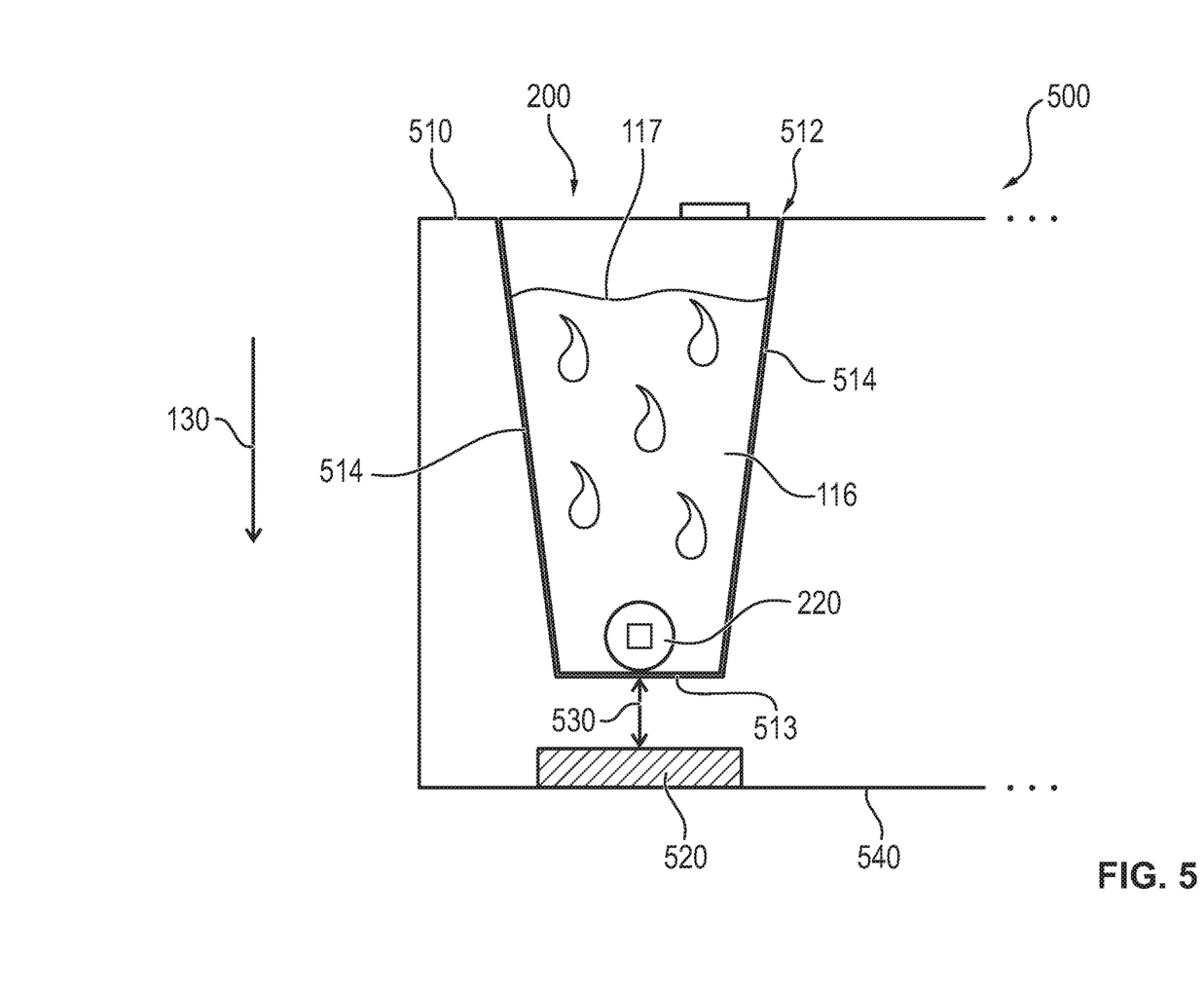
FIG. 5 is a schematic view of a first exemplary embodiment of a freezing holding device according to a third aspect of the present invention.

FIG. 5 shows a schematic view of a first exemplary embodiment of a freezing holding device 500 according to a third aspect of the present invention.

The freezing holding device 500 is configured for freezing at least one cooling element according to the present invention. In the exemplary embodiment shown, the freezing holding device 500 is configured for freezing the cooling element 200 shown in FIGS. 2a and 2b.

The freezing holding device 500 comprises for this a frame 510 and a positioning magnet 520.

The frame 510 has at least one receptacle 512 for the cooling element 200. The receptacle 512 is formed by corresponding receptacle walls 514, which likewise taper in a wedge-shaped manner towards a receptacle bottom 513 of the receptacle 512 corresponding to the wedge-shaped configuration of the cooling element 200. Due to this configuration, the receptacle 512 is arranged such that the cooling element 200 inserted into the receptacle 512 in case of a liquid coolant, i.e., before a freezing process, allows a movement of the sensor element 220 in the direction of the gravity 130 acting on the sensor element 220.

The positioning magnet 520 is arranged at the frame 510 in the area of the receptacle 512 such that the sensor element 220 in the shown liquid state of the coolant 116 is held in a starting position by means of a magnetic interaction 530 between the positioning magnet 520 and the sensor element 220 in the present embodiment. Consequently, the sensor element 220 consists of a magnetic material in the exemplary embodiment shown. This starting position is different from the final position that the sensor element 220 would assume within the cooling element 200 in the liquid state of the coolant 116 during the use of the closed-circuit respirator by a user. As described within the framework of FIGS. 2*a* and 2*b*, the sensor element 220 is configured to float on a coolant surface 117 of the liquid coolant 116 due to the buoyancy force acting in the coolant 116. The positioning magnet 520 holds the sensor element 220 against the acting buoyancy force at the housing bottom of the cooling element 200. The positioning magnet 520 is arranged on a bottom plate 540 of the freezing holding device 500 for this purpose.

The freezing holding device 500 is suitable for being arranged within a suitable freezing device and to make it possible to fix the sensor element 220 in the starting position by means of the positioning magnet 520 during a freezing time of a freezing process for freezing of the coolant 216. In this case, the suitable freezing device is typically a movable freezer, as it is used, for example, for emergency vehicles, especially for firefighting emergency vehicles, wherein the freezing holding device 500 according to the present invention is configured to be inserted into a common, movable freezer.

Figure 6:
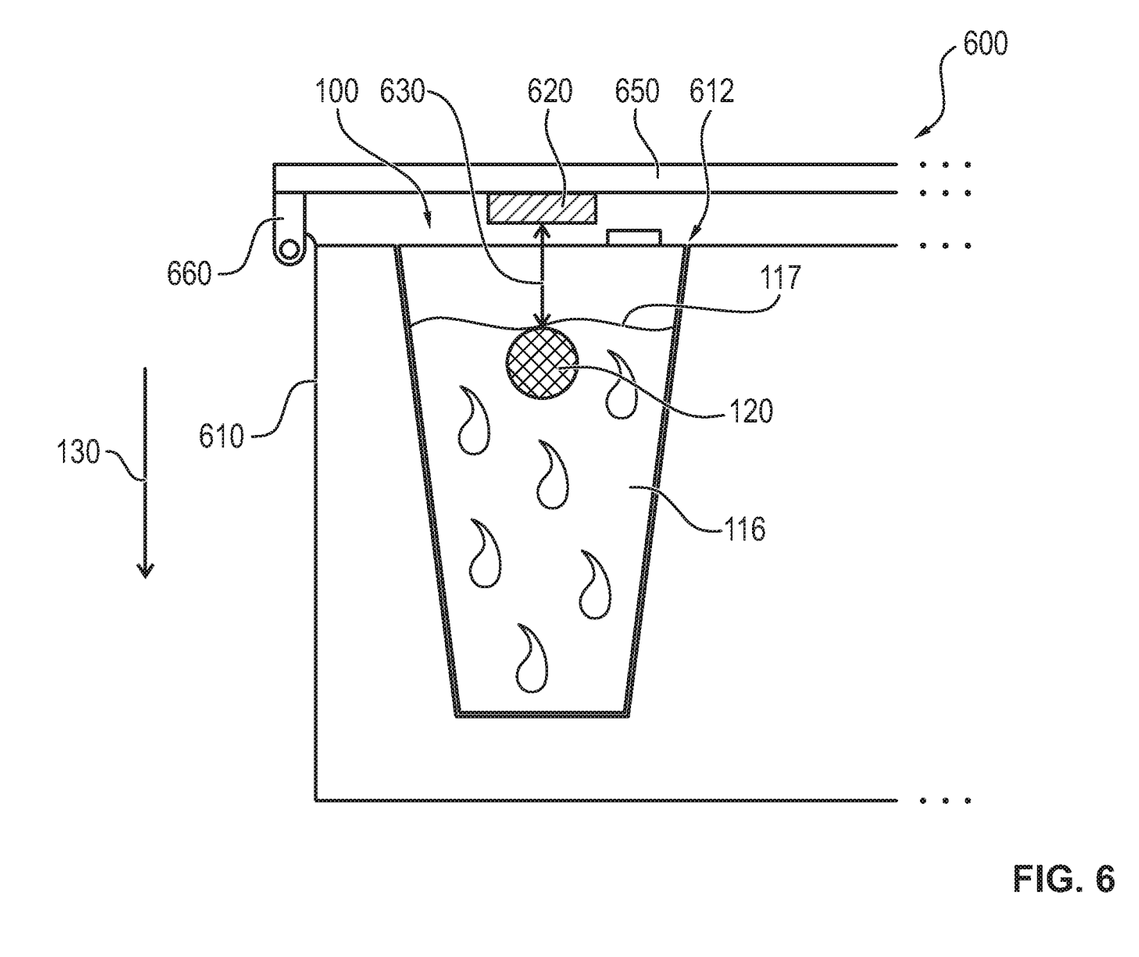
FIG. 6 is a schematic view of a second exemplary embodiment of the freezing holding device according to the third aspect of the present invention.

FIG. 6 shows a schematic view of a second exemplary embodiment of the freezing holding device 600 according to the third aspect of the present invention.

The freezing holding device 600 differs from the freezing holding device 500 by having a positioning magnet 620, which is arranged in a top plate 650 of the freezing holding device 600. Correspondingly, the freezing holding device 600 is not suitable for cooling the cooling element 200 and thus for fixing the sensor element 220 in the starting position at the housing bottom of the cooling element 200. The freezing holding device 600 is suitable for a cooling element 100, which has a sensor element that has a greater weight in the direction of the gravity 130 than the present, opposing buoyancy force in the coolant. In such a cooling element 100, the starting position of the sensor element is on a coolant surface of the coolant. The freezing holding device 500 is, by contrast, suitable for a cooling element, which has a sensor element, in which the buoyancy force present in the coolant exceeds the weight, since the starting position of the sensor element is at the housing bottom of the cooling element shown in FIG. 5 in this case.

In the present embodiment, the top plate 650 is mounted movably at the frame 610 of the freezing holding device 600 via a hinge 660. In this case, the top plate 650 can be moved between an open position and a closed position. The insertion of the cooling element into the receptacle 612 is only possible in the presence of the open position. In the present embodiment, the cooling element 100 shown in FIGS. 1*a* and 1*b* is inserted into the receptacle 612. In the closed position, the positioning magnet 620 is arranged such that the sensor element 120 in its starting position is held on the coolant surface 117 of the coolant 116 by means of a present magnetic interaction 630.

The freezing holding device according to the present invention is advantageously configured either to receive a cooling element with a sensor element floating in the coolant or to receive a cooling element with a sensor element sinking in the coolant. These two cases require each a different arrangement of the positioning magnet, as it is shown in FIG. 5 and FIG. 6.

The freezing holding device according to the present invention especially advantageously comprises a plurality of receptacles. All the cooling elements for a cooling device can thus be simultaneously frozen for a mission.

Figure 7:
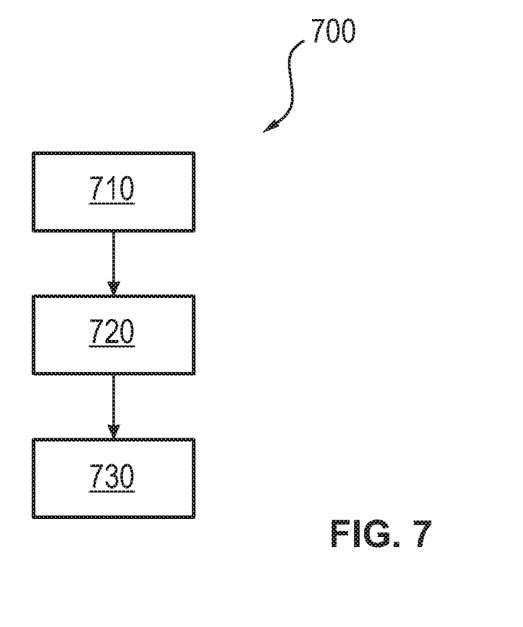
FIG. 7 is a flow chart of an exemplary embodiment of a process according to a fourth aspect of the present invention.

FIG. 7 shows a flow chart of an exemplary embodiment of a process 700 according to a fourth aspect of the present invention.

The process 700 according to the present invention for cooling a cooling element for use in a cooling device of a closed-circuit respirator has the steps shown below.

A first step 710 comprises a provision of a sensor element within a cooling element of a cooling device of the closed-circuit respirator, which cooling element is filled with coolant.

A further step 720 comprises an arrangement of the sensor element in a starting position, which is different from a final position that the sensor element assumes within the cooling element in the liquid state of the coolant during the use of the closed-circuit respirator by a user of the closed-circuit respirator.

A final step 730 comprises a cooling of the cooling element such that the coolant is cooled to below its melting point, while the sensor element remains in its starting position.

Step 710 is typically carried out during the manufacture or maintenance of the cooling element, whereas steps 720 and 730 are carried out for each cooling process of the cooling element.

Figure 8:
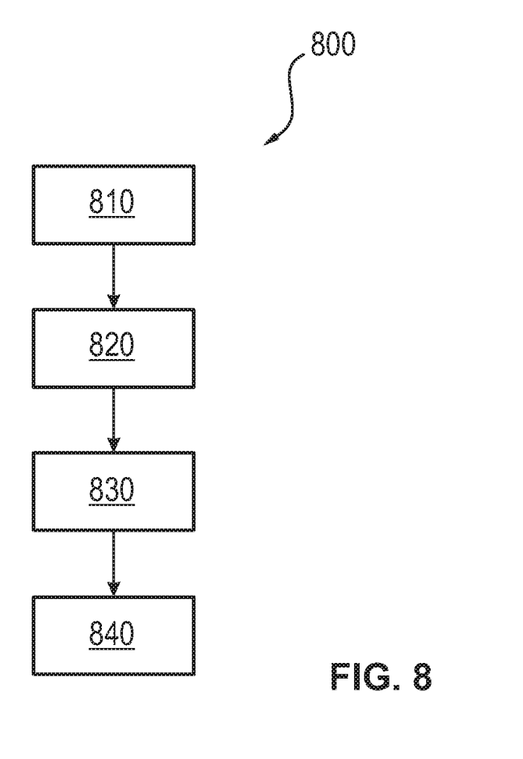
FIG. 8 is a flow chart of an exemplary embodiment of a process according to a fifth aspect of the present invention.

FIG. 8 shows a flow chart of an exemplary embodiment of a process 800 according to a fifth aspect of the present invention.

The process 800 according to the present invention for controlling a breathing gas circuit in a closed-circuit respirator has the steps shown below.

A first step 810 comprises an insertion of the cooling element into the cooling device of the closed-circuit respirator, which cooling element was cooled according to the process 700 shown in FIG. 7.

A further step 820 comprises the determination of position information and the outputting of a corresponding position signal, which implies the position information, the position information being information related to a current position of the sensor element in the cooling element.

A next step 830 comprises the receipt of the position signal, the determination of the corresponding position information, and the determination of a coolant state of the cooling device on the basis of the position information, wherein the coolant state indicates an expected, further cooling time of the cooling device.

A last step 840 comprises an outputting of a control signal based on the determined coolant state.

Step 810 is typically carried out at the beginning of the use of a correspondingly cooled closed-circuit respirator.

Steps 820, 830 and 840 are preferably carried out in this sequence during the mission at regular time intervals. The regular time intervals are typically predefined by predefined time intervals, in which the position information is polled and determined according to step 820.

While specific embodiments of the invention have been shown and described in detail to illustrate the application of the principles of the invention, it will be understood that the invention may be embodied otherwise without departing from such principles.

LIST OF REFERENCE NUMBERS

100, 200, 300, 400 Cooling element
110, 210, 310, 410 Element housing
112 Cap
114 Side wall
116 Coolant
117 Coolant surface
118, 418 Housing bottom
120, 220, 320, 420 Sensor element
130 Gravity
211 Housing guide
224 RFID tag
305, 405 Control system
306 Closed-circuit respirator
326 Information signal
340 Breathing gas circuit
345 Inhaled gas
350 Cooling device
360, 460 Detection unit
362 Transmitting device
363 Read signal
364 Antenna device
365, 465, 467 Position signal
370 Control unit
375 Control signal
380, 480 Output unit
385, 485 Optical output medium
462 Second detection unit
487 Acoustic output medium
488 Acoustic output
500, 600 Freezing holding device
510, 610 Frame
512, 612 Receptacle
513 Receptacle bottom
514 Receptacle wall
520, 620 Positioning magnet
530, 630 Magnetic interaction
540 Bottom plate
650 Top plate
660 Hinge
700, 800 Process
710, 720, 730, 810, 820, Process steps
830, 840

What is claimed is:

1. A closed-circuit respirator cooling device cooling element comprising:
   an element housing with a liquid-tight cap;
   a coolant at least partially filling the element housing, wherein the coolant has a melting point below 50° C.; and
   a sensor element arranged in contact with the coolant within the element housing such that the sensor element is movable in a direction of gravity acting on the sensor element in a liquid state of the coolant during the use of closed-circuit respirator by a user of the closed-circuit respirator.

2. The closed-circuit respirator cooling device cooling element in accordance with claim 1, wherein the sensor element is configured to sink to a housing bottom of the element housing, due to gravity acting on the sensor element in the liquid state of the coolant.

3. The closed-circuit respirator cooling device cooling element in accordance with claim 1, wherein the sensor element is configured to float on a coolant surface of the coolant due to a buoyancy force of the liquid state of the coolant on the sensor element, which buoyancy force acts against gravity, in the liquid state of the coolant.

4. The closed-circuit respirator cooling device cooling element in accordance with claim 1, wherein the sensor element comprises a passive RFID tag.

5. The closed-circuit respirator cooling device cooling element in accordance with claim 1, wherein the sensor element comprises a permanent magnet.

6. The closed-circuit respirator cooling device cooling element in accordance with claim 1, wherein the element housing further comprises a housing guide arranged within the cooling element at the element housing and configured to limit a movability of the sensor element in the coolant in the liquid state of the coolant, such that the sensor element is movable only in the direction of the gravity acting on the sensor element during the use of the closed-circuit respirator by a user of the closed-circuit respirator.

7. A control system for controlling a breathing gas circuit in a closed-circuit respirator comprising a cooling device comprising at least one cooling element arranged in a device housing of the cooling device, wherein the at least one cooling element comprises an element housing with a liquid-tight cap, a coolant at least partially filling the element housing, wherein the coolant has a melting point below 50° C., and a sensor element arranged in contact with the coolant within the element housing such that the sensor element is movable in a direction of gravity acting on the sensor element in a liquid state of the coolant during the use of the closed-circuit respirator by a user of the closed-circuit respirator, the control system comprising:
   at least one detection unit connected to the closed-circuit respirator and arranged outside of the cooling device, wherein the at least one detection unit is configured to determine position information and to output a corresponding position signal, which is indicative of the position information, wherein the position information is information related to a current position of the sensor element in the element housing of the at least one cooling element; and
   a control unit connected to the closed-circuit respirator and arranged outside of the cooling device, wherein the control unit is signal connected to the at least one detection unit and is configured to receive the position signal, to determine the corresponding position information, to determine a coolant state of the cooling device based on the position information, wherein the coolant state indicates an expected further cooling time of the cooling device, and to output a control signal based on the coolant state.

8. The control system in accordance with claim 7, wherein the determined coolant state indicates a state of aggregation of the coolant.

9. The control system in accordance with claim 8, wherein the determined coolant state indicates a movement of the sensor element from a starting position of the sensor element, which starting position is known for a frozen state of the coolant within the at least one cooling element.

10. The control system in accordance with claim 9, wherein the determined coolant state indicates a movement of the sensor element into a final position of the sensor element, which final position is known for fully melted coolant within the at least one cooling element.

11. The control system according to claim 8, further comprising;
    at least another detection unit to provide a plurality of detection units, wherein the at least another detection unit provides at least another position signal to provide a plurality of position signals, wherein the control unit is configured to determine a corresponding plurality of pieces of position information from the corresponding plurality of position signals and to determine the coolant state from the plurality of pieces of position information based on a determined movement of the sensor element.

12. The control system in accordance with claim 7, wherein the sensor element comprises a passive RFID tag and wherein the at least one detection unit is configured as an RFID reader.

13. The control system in accordance with claim 7, wherein the sensor element comprises a permanent magnet and wherein the at least one detection unit is configured as a reed relay or as a Hall sensor.

14. A freezing holding device for at least one closed-circuit respirator cooling device cooling element comprising an element housing with a liquid-tight cap, a coolant at least partially filling the element housing, wherein the coolant has a melting point below 50° C., and a sensor element arranged in contact with the coolant within the element housing such that the sensor element is movable in a direction of gravity acting on the sensor element in a liquid state of the coolant during the use of a closed-circuit respirator by a user of the closed-circuit respirator, the freezing holding device comprising:
    a frame with at least one receptacle for the at least one cooling element, wherein the at least one receptacle is arranged such that the at least one cooling elementwith liquid coolant inserted into the at leas tone receptable allows a movement of the sensor element in the direction of the gravity acting on the sensor element;
    a positioning magnet arranged at the frame in an area adjacent to the at leas tone receptacle such that the sensor element is held in a starting position in a liquid state of the coolant via a magnetic force acting between the positioning magnet and the sensor element, which starting position is different from a final position that the sensor element assumes within the at least one cooling element in the liquid state of the coolant during the use of the closed-circuit respirator by a user of the closed-circuit respirator, wherein the freezing holding device is configured to be arranged within a suitable freezing device and for making possible a fixing of the sensor element in the starting position due to the positioning magnet during a freezing time of a freezing process for freezing the coolant of the at least one cooling element.

15. The freezing holding device in accordance with claim 14, wherein the positioning magnet is arranged at a bottom plate or at a top plate of the freezing holding device.

16. The freezing holding device in accordance with claim 15, wherein:
    the top plate is mounted movably between an open position and a closed position at the frame of the freezing holding device; and
    the top plate is configured such that insertion of the at least one cooling element into the at least one receptacle is possible only in the open position of the top plate; and
    the positioning magnet is arranged adjacent to the at least one receptacle only in the closed position of the top plate such that the sensor element is held in the starting position in the closed position of the top plate.

17. A process for cooling a cooling element for use in a cooling device of a closed-circuit respirator, the process comprising the steps of:
    providing a sensor element within a cooling element of a cooling device of the closed-circuit respirator, which cooling element is filled with coolant;
    arranging the sensor element in a starting position, which is different from a final position that the sensor element assumes within the cooling element in a liquid state of the coolant upon use of the closed-circuit respirator by a user of the closed-circuit respirator; and
    cooling of the cooling element such that the coolant is cooled to below a melting point of the coolant, while the sensor element remains in the starting position.

18. The process according to claim 17, further comprising controlling a breathing gas circuit in a closed-circuit respirator, wherein the controlling comprises the steps of:
    inserting the cooling element into the cooling device of the closed-circuit respirator, which cooling element was cooled with said step of cooling;
    determining position information and outputting of a corresponding position signal, which implies the position information, wherein the position information is information related to a current position of the sensor element in the cooling element;
    receiving the position signal determination of the corresponding position information, and determining a coolant state of the cooling device on the basis of the position information, wherein the coolant state indicates an expected, further cooling time of the cooling device; and
    outputting a control signal based on the coolant state.

* * * * *